United States Patent [19]
Trauner et al.

[11] Patent Number: 5,913,884
[45] Date of Patent: Jun. 22, 1999

[54] INHIBITION OF FIBROSIS BY PHOTODYNAMIC THERAPY

[75] Inventors: Kenneth Trauner, Boston; Tayyaba Hasan, Arlington; Michael R. Hamblin, Revere, all of Mass.

[73] Assignee: The General Hospital Corporation, Boston, Mass.

[21] Appl. No.: 08/741,816

[22] Filed: Oct. 31, 1996

Related U.S. Application Data

[60] Provisional application No. 60/026,315, Sep. 19, 1996.
[51] Int. Cl.[6] .................................................. A61B 17/00
[52] U.S. Cl. .................................................. 607/88; 607/92
[58] Field of Search ...................................... 607/88; 1/92

[56] References Cited

U.S. PATENT DOCUMENTS

| | | | |
|---|---|---|---|
| 5,368,841 | 11/1994 | Trauner et al. | 424/9 |
| 5,405,369 | 4/1995 | Selman et al. | 607/88 |

OTHER PUBLICATIONS

Bachor et al., "Mechanism of Photosensitization by Microsphere–Bound Chlorin $e_6$ in Human Bladder Carcinoma Cells", Cancer Research 51:4410–4414, 1991.

Bachor et al., "Photosensitized Destruction of Human Bladder Carcinoma Cells Treated With Chlorin $e_6$—Conjugated Microspheres", Proc. Natl. Sci. USA 88:1580–1584, 1991.

Batlle, "Porphyrins, Porphyrias, Cancer and Photodynamic Therapy—A Model Carcinogenesis", J. Photochem. Photobiol. B: Biol. 20:5–22, 1993.

Beems et al., "Photosensitizing Properties of Bacteriochlorophyllin α and Bateropcj; prom α. Two Derivatives of Bacteriochlorophyll α", Photochemistry and Photobiology 46:639–643, 1987.

Detmar et al., "Keratinocyte–Derived Vascular Permeability Factor (Vascular Endothelial Growth Factor) Is A Potent Mitogen for Dermal Microvascular Endothelial Cells", J. Investigative Dermatology 105:44–50, 1995.

Dougherty et al., "Photodynamic Therapy of Neoplastic Disease, vol. 1", pp. 1–19, CRC Press, (Kessel, ed) Boca Raton, 1989.

Evans et al., "Effect of Photodynamic Therapy on Tumor Necrosis Factor Production by Murine Macrophages", J. Natl. Cancer Institute 82:34–39, 1990.

Gurinovich et al., "Photodynamic Activity of Chlorin $e_6$ ethylenediamide in Vitro and in Vivo", J. Photochem. Photobiol. B: Biol., 13:51–57, 1992.

Hamblin et al., "Photosensitizer Targeting in Photodynamic Therapy I. Conjugates of Haematoporphyrin with Albumin and Transferin", J. Photochem. & Photobiol. B: Biol. 26:45–56, 1994.

Hamblin et al., "Photosensitizer Targeting in Photodynamic Therapy II. Conjugates of Haematoporphyrin with Serum Lipoproteins", J. Photochem. & Photobiol. B: Biol. 26:147–157, 1994.

Kessel, "Interactions Between Porphyrins and Mitochodrial Benzodiazepine Receptors", Cancer Letters 39:193–198, 1988.

Kessel, "Photosensitization With Derivatives of Chlorophyll", Photochem. & Photobiol. 49:157–160, 1989.

Kessel, "Determinants of Photosensitization by Purpurins" Photochem. & Photobiol. 50:169–174, 1989.

Koren et al., "Photodynamic Therapy—An Alternative Pathway in the Treatment of Recurrent Breast Cancer", Intl. J. Radiation Oncology Biol. Phys. 28:463–466, 1994.

Kreimer–Birnbaum, "Modified Porphyrins, Chlorins, Phthalocyanines, and Purpurins: Second–Generation Photo–sensitizers for Photodynamic Therapy", 26:157–173, 1989.

Molpus et al., "Intraperitoneal Photodynamic Therapy of Human Epithelial Ovarian Carcinomatosis in a Xenograft Murine Model", Cancer Research 56:1075–1082, 1986.

Morgan et al., Metallopurpurins and Light: Effect on Transplantable Rat Bladder Tumors and Murine Skin, Photochemistry and Photobiology, 51:589–592, 1990.

Obochi et al., "Photodynamic Therapy (PDT) as a Biological Modifier", SPIE 2675:122–133, 1996.

Yamamoto et al., "Activation of Mouse Macrophages by in Vivo and in Vitro treatment with a Cyanine Dye, Lumin", J. Photochem. Photobiol. 13:295–306, 1992.

Yamamoto et al., "Effectiveness of Photofrin II In Activation of Macrophages and in Vitro Killing of Retinoblastoma Cells", Photochemistry and Photobiology 60:160–164, 1994.

*Primary Examiner*—Cecilia J. Tsang
*Assistant Examiner*—Patrick R. Delaney
*Attorney, Agent, or Firm*—Fish & Richardson P.C.

[57] ABSTRACT

Disclosed is a method for modulating wound healing in a mammal. The method includes the steps of: (a) administering a photosensitizer to a mammal that has an unhealed or partially-healed wound; (b) waiting for the photosensitizer to reach an effective tissue concentration at the wound site; (c) photoactivating the photosensitizer by delivering specifically to the wound site light of a effective wavelength and intensity, for an effective length of time. The modulation of wound healing can include hastening healing by administering a low dose of photodynamic therapy. Alternatively, the modulation can include inhibiting fibrosis by administering a high dose of photodynamic therapy. The photosensitizer can be targeted, for example, to macrophages or myofibroblasts. Targeting can be by conjugation to a targeting moiety such as a protein, peptide or microparticle.

14 Claims, 1 Drawing Sheet

FIG. 1

INHIBITION OF FIBROSIS BY PHOTODYNAMIC THERAPY

CROSS-REFERENCE TO RELATED APPLICATION

This application claims benefit from U.S. provisional application Ser. No. 60/026,315, filed Sep. 19, 1996.

FIELD OF THE INVENTION

This invention relates to wound healing and photodynamic therapy.

BACKGROUND OF THE INVENTION

Dysfunctional healing CAN involve a slowing of the process, which can lead to indolent and chronic wounds. Such slowing can be due to factors such as hemorrhagic shock, infection, immune suppression, or prolonged psychological distress. Alternatively, dysfunctional healing can involve a hyperproliferative response, which can lead to, e.g., post-surgical adhesions.

Macrophages are central to the complex process of wound healing, which involves removal of dead tissue, formulation of granulation tissue, neovascularization, stimulation of locomotion and proliferation of fibroblasts and keratinocytes, and production of collagen types I and III. Photodynamic therapy can destroy large amounts of tissue with a good healing response and good cosmetic result (Koren et al, *Int. J. Radiat. Oncol. Biol. Phys.* 28:463–466 (1994)). Photodynamic therapy can be used either to stimulate or suppress cellular responses such as cytokine release and immune function. Whether the photodynamic therapy causes stimulation or suppresion depends on the dosage. Low dose photodynamic therapy stimulates cytokine release and immune function, while high dose photodynamic therapy suppresses those processes (Obochi et al., *SPIE Proc.* 2675:122–131 (1996); Yamamoto et al., *Photochem. Photobiol.* 60:160–164 (1994)).

Photodynamic therapy has major effects on macrophages. Low dose photodynamic therapy activates macrophages. This enhances their cytotoxicity against tumor cells (Yamamoto et al., *Photobiol. B* 13:295–306 (1992)). High dose photodynamic therapy leads to production of TNF alpha, and eventually, macrophage death (Evans et al., *J. Natl. Cancer Inst.* 82:34–39 (1990)).

Fibrosis is a response to injury in which new extracellular matrix is rapidly laid down producing dense bands of collagen that are the microscopic hallmark of scarring. The extent and duration of fibrosis often far exceeds the apparent need for wound healing, causing hypertrophic scars and contractures that limit function or distort anatomy. In the peritoneum, joints, tendon sheaths, or essentially any body space with an epithelial lining, injury and fibrosis can lead to adhesions which bind tissues together. Scars remain metabolically hyperactive long after injury, both producing and degrading extracellular matrix at a rate many times that of uninjured tissue.

The initiation and control of many concerted processes responsible for wound healing are governed by molecules which direct cell activity such as cytokines, growth factors, and adhesion molecules. In particular, the extracellular matrix growth factors TGF-$\beta$, platelet derived growth factor (PDGF), and basic fibroblast growth factor (bFGF) appear to initiate and/or sustain fibrosis. Specifically TGF-$\beta$ appears to be the dominant cytokine governing the aggressiveness of the scarring response. TGF$\beta$ has been implicated in hepatic fibrosis, pulmonary fibrosis, scleroderma, and keloids. It stimulates collagen and fibronectin formation, suppresses collagenase and induces production of collagenase inhibitors. Increased TGF-$\beta$ levels, increasing scarring, and more rapid healing responses are associated with disorientation and thinning of type I collagen fibers with abnormal production of proteoglycans and glycosaminoglycans in wound extracellular matrix.

Photodynamic therapy has been used to treat cancer. See, e.g., Dougherty et al., *In Photodynamic Therapy of Neoplastic Disease,* (Kessel, ed.), CRC Press, Boca Raton, Fla. (1989). Photodynamic therapy has also been used for destruction of the synovium in the treatment of rheumatoid arthritis (U.S. Pat. No. 5,368,841).

SUMMARY OF THE INVENTION

The invention features a method for modulating the healing of a wound in a mammal. The method includes the steps of: (a) administering an effective amount of a photosensitizer to a mammal that has an unhealed or partially-healed wound; (b) waiting for a time period wherein the photosensitizer reaches an effective tissue concentration at the wound site; (c) photoactivating the photosensitizer at the wound site by delivering specifically to the wound site light of a effective wavelength and intensity, for an effective length of time. The modulation of wound healing can include hastening healing by administering a low dose of photodynamic therapy. Alternatively, the modulation can include inhibiting fibrosis by administering a high dose of photodynamic therapy.

Photosensitizers include members of the following classes of compounds: porphyrins, chlorins, bacteriochlorins, purpurins, phthalocyanines, naphthalocyanines, texaphyrins, and non-tetrapyrrole photosensitizers. Specific examples include Photofrin, benzoporphyrin derivative, tin etiopurpurin, sulfonated chloroaluminum phthalocyanine and methylene blue. The photosensitizer can be targeted, for example, to macrophages or myofibroblasts, by conjugation to a targeting moiety such as a protein, peptide, or microparticle. Administration of the photosensitizer can be local or systemic. For systemic administration, the preferred dosage is between about 0.1 mg/kg and about 50 mg/kg. More preferably, it is at a dosage level between about 0.5 mg/kg and about 10 mg/kg. In other embodiments of the invention, the administration of the photosensitizer is local. Local administration can be perilesional or topical.

Light for photoactivation of the photosensitizer can be delivered to the wound site using various light sources and various means of delivery. For superficial wounds or open surgical wounds, suitable light sources include broadband conventional light sources, broad arrays of LEDs, and defocussed laser beams. For deeper wound sites, including those in intracavitary settings, useful means of light delivery include optical fiber devices and transillumination.

The invention can be used prophylactically, i.e., before surgery, to modulate the healing of surgical wounds. Such modulation can be used to reduce surgical adhesions, e.g., intrapleural adhesions, intraperitoneal adhesions, tendon sheath adhesions, and intraarticular adhesions.

As used herein, "low dose" photodynamic therapy means a dose sufficient to kill from 0% to about 10% of all cells exposed to the photoactiviting light if the photosensitizer is untargeted, or from 0% to about 10% of the targeted cells exposed to the photoactiviting light, if the photosensitizer is targeted. As used herein, "high dose" photodynamic therapy means a dose sufficient to kill from about 10% to about 90% of all cells exposed to the photoactivating light if the photosensitizer is untargeted, or from about 10% to about 90% of the targeted cells exposed to the photoactivating light, if the photosensitizer is targeted.

As used herein, "high dose" photodynamic therapy means a dose sufficient to kill from about 30% to about 100% of all cells exposed to the photoactivating light if the photosensitizer is untargeted, or from about 30% to about 100% of the targeted cells exposed to the photoactivating light, if the photosensitizer is targeted. The dose of photodynamic therapy is calculated as the product of photosensitizer dose and photoactivating light dose. Thus, photodynamic therapy dose can be adjusted by adjusting the photosensitizer dose, photoactivating light dose, or both.

As used herein, "photoactivation" means a light-induced chemical reaction of a photosensitizer which produces a biological effect.

As used herein, "photosensitizer" means a chemical compound that produces a biological effect upon photoactivation, or a biological precursor of a compound that produces a biological effect upon photoactivation.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present document, including definitions, will control. Unless otherwise indicated, materials, methods, and examples described herein are illustrative only and not intended to be limiting.

Various features and advantages of the invention will be apparent from the following detailed description and from the claims.

BRIEF DESCRIPTION OF THE DRAWING

FIG. 1 is a graph of haematoporphyrin uptake per mg of cell protein, as a function of the concentration of haematoporphyrin equivalents. This graph summarizes the results of experiments performed to demonstrate selective targeting of low density lipoprotein-haematoporphyrin conjugates (LDL-HP) to macrophages. Solid line, LDL-HP taken up by fibroblasts; broken line with open circles, LDL-HP taken up by macrophages; broken line with open squares, unconjugated haematoporphyrin taken up by macrophages.

DETAILED DESCRIPTION

The present invention involves applying photodynamic therapy ("PDT") to an unhealed or partially healed wound. In general, photodynamic therapy involves administration of a photosensitizer to a patient, followed by photoactivation of the photosensitizer, to produce a cytotoxic effect. In the present invention, photoactivating light is delivered specifically to an unhealed or partially-healed wound, where the biological effect modulates wound healing.

The modulation of wound healing can be achieved according to this invention by modulating macrophage function, myofibroblast function, endothelial cell function, or any combination thereof, through photodynamic therapy at a wound site. Preferaby, the photodynamic therapy includes targeting a photosensitizer to macrophages and myofibroblasts. Targeting can be accomplished, for example, by conjugating the photosensitizer to a targeting moiety that binds to a receptor on the macrophage or myofibroblast surface, e.g., an LDL receptor or a "scavenger" receptor. Alternatively, macrophage targeting can be accomplished by exploiting the phagocytosis that characterizes macrophages and myofibroblasts. The photosensitizer can be conjugated to a microparticle, e.g., a 1 μm polystyrene microsphere (Polysciences, Inc.). Such photosensitizer-microparticle conjugates are taken up selectively by macrophages and myofibroblasts, due to phagocytotic activity of those cell types. A photosensitizer-microparticle conjugate can be produced by known methods, e.g., those described in Bachor et al., *Proc. Natl. Acad. Sci. USA* 88:1580–1584 (1991).

Fibrosis is a complex process involving different cell types such as fibroblasts, myofibroblasts, and macrophages. Fibrosis also involves interactions between cells by means of biologically active molecules such as growth factors, cytokines, and cell adhesion molecules. Therefore, fibrosis can be advantageously inhibited according to the present invention in various ways. For example, in one embodiment of the invention inhibition of fibrosis results from localized killing of cells involved in fibrosis, e.g., macrophages. Such localized killing can be rendered selective for a particular cell type through the use of a targeted photosensitizer. Preferably, the inhibition of fibrosis results from localized inactivation of extracellular growth factors or cytokines. More preferably, it results from inactivation of TGF-β or bFGF. Inhibition of fibrosis according to this invention can involve one or more of the following: decreased collagen production, modified collagen cross-linking, changes in remodeling of the extracellular matrix, and breakdown of collagen.

Inhibiting fibrosis according to the present invention is a useful adjunct to surgical practice in general. Post operative scarring and fibrosis in the healing of surgical incisions is a common complication from surgery. In hand surgery, excessive scarring of skin can cause joint contracture. Any joint subjected to surgery or injury is at risk of arthrofibrosis. Tendon repair surgery can result in adhesions surrounding the tendon repair. In reconstructive orthopaedic surgery, stiffness and decreased range of motion often follow surgery and compromise clinical outcome. Arthrofibrosis is a frequent complication of procedures such as anterior cruciate ligament reconstruction and total hip replacement. Intraabdominal adhesions are a frequent complication following abdominal surgery. This invention is useful in all such surgical situations. The present invention can also be used to inhibit fibrosis and excessive scarring in the healing of wounds other than surgical incisions.

Photosensitizer

The photosensitizer is a chemical compound that produces a biological effect upon photoactivation, or a biological precursor of a compound that produces a biological effect upon photoactivation. The photosensitizer must have a sufficiently low toxicity to permit administration to the patient with a medically acceptable level of safety. Preferably, the photosensitizer is essentially nontoxic, except for the desired cytotoxic effect produced locally, upon photoactivation.

Various photosensitizers are known and can be used in the practice of this invention. Photosensitizers typically have chemical structures that include mutiple conjugated rings that allow for light absorption and photoactivation. They differ in the properties of light absorption and fluorescence, biodistribution, temporal uptake, clearance, and mechanisms of photoactivatable cytotoxicity. Classes of photosensitizers include hematoporphyrins (Batlle, *J. Photochem. Photobiol. B-Biol.* 20:5–22 (1993); Kessel, *Cancer Let.*

39:193–198 (1988)), uroporphyrins, phthalocyanines (Kreimer-Birnbaum, *Seminars in Hematology* 26:157–173 (1989)), purpurins (Morgan et al., *Photochem. Photobiol.* 51:589–592 (1990); Kessel, *Photochem. Photobiol.* 50:169–174 (1989)), acridine dyes, bacteriochlorophylls (Beems et al., *Photochem. Photobiol.* 46:639–643 (1987); Kessel et al., *Photochem. Photobiol.* 49:157–160 (1989)), and bacteriochlorins (Gurinovich et al., *J. Photochem. Photobiol. B-Biol.* 13:51–57 (1992)). Specific examples of suitable photosensitizers are listed in Table 1.

TABLE 1

Photosensitizers

1. Photofrin®
2. Synthetic diporphyrins and dichlorins
3. Hydroporphyrins, e.g., chlorins and bacteriochlorins of the tetra(hydroxyphenyl) porphyrin series
4. phthalocyanines
5. O-substituted tetraphenyl porphyrins (picket fence porphyrins)
6. 3,1-meso tetrakis (o-propionamido phenyl) porphyrin
7. Verdins
8. Purpurins, e.g., tin and zinc derivatives of octaethylpurpurin (NT2), and etiopurpurin (ET2)
9. Chlorins, e.g., chlorin e6, and mono-l-aspartyl derivative of chlorin e6
10. Benzoporphyrin derivatives (BPD), e.g., benzoporphyrin monoacid derivatives, tetracyanoethylene adducts of benzoporphyrin, dimethyl acetylenedicarboxylate adducts of benzoporphyrin, Diels-Adler adducts, and monoacid ring "a" derivative of benzoporphyrin
11. Low density lipoprotein mediated localization parameters similar to those observed with hematoporphyrin derivative (HPD)
12. sulfonated aluminum phthalocyanine (Pc)
    sulfonated AlPc
    disulfonated (AlPcS$_2$)
    tetrasulfonated derivative
    sulfonated aluminum naphthalocyanines
    chloroaluminum sulfonated phthalocyanine (CASP)
13. zinc naphthalocyanines
14. anthracenediones
15. anthrapyrazoles
16. aminoanthraquinone
17. phenoxazine dyes
18. phenothiazine derivatives
19. chalcogenapyrylium dyes cationic selena and tellurapyrylium derivatives
20. ring-substituted cationic PC
21. pheophorbide α
22. hematoporphyrin (HP)
23. protoporphyrin
24. 5-amino levulinic acid Photosensitizers include members of the following classes of compounds: porphyrins, chlorins, bacteriochlorins, purpurins, phthalocyanines, naphthalocyanines, texaphyrines, and non-tetrapyrrole photosensitizers. Specific examples are Photofrin, benzoporphyrin derivative, tin etiopurpurin, sulfonated chloroaluminum phthalocyanine and methylene blue. BPD is a second generation porphyrin photosensitizer that diffuses rapidly from microvasculature and disseminates throughout a joint. In addition, BPD has a low affinity for chondrocytes and articular cartilage following systemic or intra-articular injection. CASPc, a phthalocyanine inactivates growth factors TGF-β and bFGF.

A single photosensitizer compound can be used alone in the practice of this invention. Alternatively, two or more photosensitizers can be used in combination, provided that light of a effective wavelength for each photosensitizer in the combination is used in the photoactivation step.

An alternative to administration of the photosensitizer compound itself, is administration of a photosensitizer precursor molecule. This approach is illustrated by the use of 5-aminolevulinic acid, which causes endogenous production of the photosensitizer protoporphyrin IX (Morgan et al., *J. Med. Chem.* 32:904–908 (1989).

The mechanism of the biological effect produced upon photoactivation need not be of a particular type, as long as the desired inhibition of fibrosis is achieved. The mechanism of the cytotoxic effect will depend upon the particular photosensitizer used. Typically, the cytotoxic effect results from the generation of a short-lived, highly reactive, diffusible species such as singlet oxygen or free radicals. Singlet oxygen or free radicals can then react with double bonds and initiate free radical chain reactions which can inactivate biologically active molecules such as growth factors or cytokines. Such a reaction process can also degrade or disorganize biological membranes of cells that participate directly or indirectly in fibrosis.

The photosensitizer can be chosen, or chemically modified, to optimize its usefulness in specific treatment situations. For example, the photosensitizer can be chemically modified to reduce its interaction with articular cartilage, when used to inhibit arthrofibrosis. This could be done by eliminating a positive charge to reduce association with negatively charged proteoglycans of articular cartilage. For targeting to a particular organ or tissue, the photosensitizer can be chemically conjugated to a targeting moiety such as a monoclonal antibody.

The photosensitizer can be formulated to optimize its usefulness for particular applications. For example, it can be formulated in a salve or gel for topical application. It can be formulated for parenteral administration or oral administration. Appropriate formulation can be carried out by one of ordinary skill in the art, without undue experimentation.

Administration of the photosensitizer can be local or systemic. The administration can be by any suitable route, including topical, intravenous, intraarticular, subcutaneous, intramuscular, intraventricular, intracapsular, intraspinal, intraperitoneal, topical, intranasal, oral, buccal, rectal or vaginal. The preferred route of administration will depend on the size and nature of the wound, and on the location of the wound.

Parenteral formulations may be in the form of liquid solutions or suspensions; for oral administration, formulations may be in the form of tablets or capsules; and for intranasal formulations, in the form of powders, nasal drops, or aerosols.

Methods well known in the art for making formulations are to be found in, for example, "Remington's Pharmaceutical Sciences." Formulations for parenteral administration may, for example, contain as excipients sterile water or saline, Cremophor EL, polyalkylene glycols such as polyethylene glycol, oils of vegetable origin, or hydrogenated naphthalenes biocompatible, biodegradable lactide polymer, or polyoxyethylene-polyoxypropylene copolymers may be used to control the release of the present factors. Other potentially useful parenteral delivery systems for the factors include ethylene-vinyl acetate copolymer particles, osmotic pumps, implantable infusion systems, liposomes, and antibody conjugates. Formulations for inhalation may contain as excipients, for example, lactose, or may be aqueous solutions containing, for example, polyoxyethylene-9-lauryl ether, glycocholate and deoxycholate, or may be oily solutions for administration in the form of nasal drops, or as a gel to be applied intranasally. Formulations for parenteral administration may also include glycocholate for buccal administration, methoxysalicylate for rectal administration, or citric acid for vaginal administration.

Where the size, nature, and location of the wound being treated renders local administration of the photosensitizer feasible, local administration is preferred over systemic administration. Local adminstration generally reduces the likelihood of unwanted side effects. In addition, it typically permits greater control over photosensitizer concentration at the wound site.

Photoactivation

In preferred embodiments of the invention, the method includes a waiting step between the step of administering the photosensitizer and the step of photoactivating the photosensitizer. The waiting step is designed to allow the photosensitizer to reach an optimal tissue concentration at the wound site, prior to photoactivation. The length of the waiting step will depend on factors such as the route by which the photosensitizer is administered, the location of the wound, and the speed with which the photosensitizer moves in the body. Typically, the waiting step will be longer when the photosensitizer is administered systemically.

The wound site is exposed to light of an effective wavelength and intensity, for an effective length of time. What wavelength, or range of wavelengths, is effective will depend on the photosensitizer(s) used. Wavelength specificity for photoactivation depends on the molecular structure of the photosensitizer. Photoactivation occurs with sub-ablative light doses.

Preferably, delivery of the light used to photoactivate the photosensitizer is limited to the wound site and the area immediately surrounding the wound site. This minimizes undesirable cytotoxic side effects.

The light for photoactivation can be produced and delivered to the wound site by any suitable means. For example, the light can be delivered via optical fibers threaded through small gauge hypodermic needles. Alternatively, the light can be provided extracorporeally by transillumination. Some photosensitizing compounds can be activated by near infrared and longer wavelength visible light. This allows deeper tissue penetration of the photoactivating light, thereby facilitating transillumination. Optical fibers can be passed via arthroscopes with direct visual targeting and activation of the compounds. Optical fibers can also be passed directly via small gauge hypodermic needles. Light can also be transmitted via percutaneous instrumentation using optical fibers or cannulated waveguides. Transillumination can be performed using a variety of devices. The devices can utilize laser or non-laser sources, i.e. lightboxes or convergent light beams. Photoactivation can also be performed by open arthrotomy.

EXPERIMENTAL INFORMATION

Selective Uptake of LDL-HP by Macrophages

Figure 1:
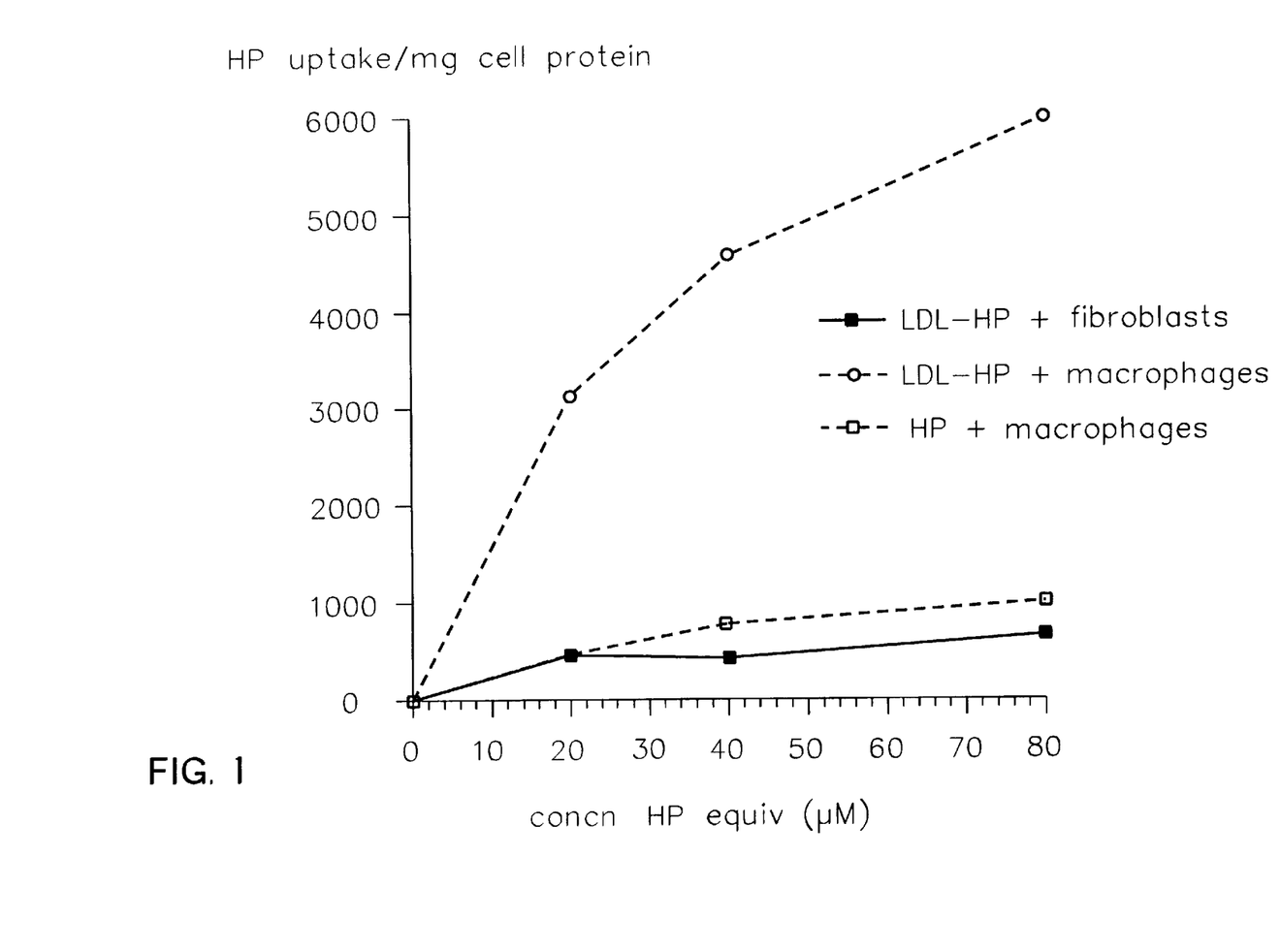

Experiments have been carried out to demonstrate selective uptake of low density lipoprotein-haematoporphyrin conjugates (LDL-HP) by J774 macrophages, as compared to 3T3 fibroblasts. As a negative control, uptake of unconjugated HP by the macrophages was also measured. The macrophage uptake of LDL-HP was approximately 9-fold greater than macrophage uptake of unconjugated HP (FIG. 1). Macrophage uptake of LDL-HP was approximately 13-fold greater than fibroblast uptake of LDL-HP (FIG. 1).

In the LDL-HP uptake experiments, LDL-HP was prepared essentially as described in Hamblin et al, *J. Photochem. Photobiol. B* 26:45–56 (1994)). Heamatoporphyrin N-hydroxysuccinamide ester (HP-NHS) was prepared by mixing 20 umol HP with 40 um NHS and 40 umol DCC in 2 ml dry dimethyl sulfoxide, and leaving the mixture in the dark at room temperature overnight. Conjugation to low density lipoprotein was performed by dissolving 10 mg of protein in 2 ml of 0.1 M HP-NHS solution. The solution was mixed thoroughly and allowed to stand overnight at room temperature. All subsequent operations with conjugates were carried out in subdued light. The crude conjugation reaction product was applied to a column of Sephadex G50 and eluted with 5 mM $NaHCO_3$ (pH 8). The brown band of protein conjugate rapidly separated from the red band of free porphyrin. The conjugates were stored at $-20°$ C., in solutions containing 10–20% glycerol.

The cell lines were grown in 1:1 Dulbecco's modified Eagle medium (DMEM)-Hams F12 medium supplemented with glutamine, antibiotics, and 10% fetal calf serum. Experimental cultures were grown to semi-confluence in 24-well tissue culture plates containing 1 ml medium per well. The medium was replaced and conjugates were added in phosphate-buffered saline (PBS). Free photosensitizer was added in a small volume (5 $\mu$l) of dimethyl sulfoxide.

At the end of incubation, the medium was removed, the cells were washed with PBS (3×1 ml) and incubated with trypsin-EDTA for 10 minutes (3T3 fibroblasts) or one hour (J774 macrophages). The cells were centrifuged, and the pellet (usually fluorescent under long-wave UV) was dissolved in 1 ml of a mixture of 1% sodium dodecylsulfate (SDS) and 0.1 M NaOH. The fluorescence of the cell extract was measured (emission, 632 nm; excitation 412 nm) and the protein content was determined by the Lowry method. Results were expressed as fluorescence units per mg of cell protein. One fluorescence unit per milligram of protein is approximately equal to 1.7 pmol porphyrin per milligram of cell protein, i.e., about $10^6$ molecules porphyrin per cell.

The following experimental protocols provide additional guidance enabling one of ordinary skill in the art to practice the present invention.

Macrophage Targeted Photodynamic Regulation of Wound Healing

In this protocol, 64 hairless rats receive multiple surgical incisions to their backs. Incisions are applied at 2 time points prior to, and 1 time point after, application of photodynamic therapy. The photodynamic therapy entail systemic or local photosensitizer administration followed by regional light therapy.

For each treatment, either for surgical incisions, PDT treatment, or biopsy, animals are sedated with general anesthesia. Anesthesia is induced using an intramuscular injection of either Ketamine (80 mg/kg), or Xylazine (12 mg/kg). Anaesthesia is determined approximately 15 minutes post-injection by the absence of spontaneous movement, with maintenance of spontaneous respiration. The assessment of deep anaesthesia is determined every 15 minutes by gentle touching of the edge of the sclera with a cotton swab to look for the blinking response. Reinjection of the anaesthetic is done only if necessary. During the experiment, care is taken to keeping the animals warm, such as by placing them on a warm table. Postoperatively, pain is monitored by observation of behavior. Pain control is provided with buprenorphine 0.03 mg/kg SQ, q 12 hrs.

At 3 days prior to, one hour prior to, and one hour after photodynamic treatment, a series of full thickness incisions are made with a #10 scalpel blade on the back of each animal. Incisions are 25 mm in length, and spaced 1 inch apart. At time 0, rats 1–24 receive systemic injection of varying concentrations (0.5 mg/kg to 10 mg/kg) of CASP via a 30 gauge needle into the tail vein. Wounds are irradiated with 25, 50 or 100J laser energy at a wavelength of 675 nm at 5, 180 minutes, and 24 hours post injection. Animals 25–48 are treated with topical application of methylene blue 5 minutes before, and one hour before, photo activation. Using similar laser treatment parameters, 660 nm light is applied to the incision sites. Animals 49–56 are treated with systemic injections of BPD-MA (0.5 mg/kg to 10 mg/kg) and 692 nm light. Animals 57–64 are treated with systemic injections of $SnEt_2$ (0.5 mg/kg to 5 mg/kg) and 700 nm light. Incisions sites not exposed with light serve as controls. Dark toxicity controls are performed for each photosensitizer.

At 1 day, one week, 2, 4, 8 and 10 weeks post treatment, incisions are harvested as 5 mm×25 mm specimens and serially sectioned into 1 mm thick specimens. Biopsy sites are closed with interrupted 3-0 nylon suture. Wounds at each time point prior to biopsy are photographed and degree of scarring evaluated by visual analogue and categorical scales. For each time point, specimens are fixed, sectioned and stained with H+E for histologic evaluation. Immunofluorescence staining of histologic sections are performed for growth factors and their receptors, to determine the depth of effect below the skin surface. Instron testing on three 1 mm thick strips are performed to characterize tensile strength of the wound repair. TGF-$\beta$, bFGF, and PDGF tissue concentrations are quantified by RIA on specimens weighed immediately post harvest. mRNA levels, reflecting growth factor production, are assessed by Northern blot techniques or RNase protection assays, if greater sensitivity is required. Type I collagen content is measured by hydroxyproline assay. Collagen synthesis is assayed by measurement of tritiated hydroxyproline incorporation. GAG content is evaluated by carbazole biochemical assay. All animals are euthanized at 10 weeks post treatment by $CO_2$ inhalation.

Photodynamic Inactivation of Extracellular Growth Factors in Wound Healing

Three targeting moieties and one photosensitizer are used. Conjugates are prepared using LDL (ligand for modified LDL receptor), maleylated BSA (ligand for scavenger receptor), polystyrene nanospheres (100–200 nm dia.) (ligand for macrophage phagocytosis) and the photosensitizer, ce6. Conjugates are characterized by SDS polyacrylamide gel electrophoresis, reverse phase HPLC, fluorescence and absorption spectrophotometry.

Quantitative binding studies and cellular fluorescence imaging are carried out using a two photon fluorescence confocal microscopy system. Four cell lines are used for in vitro studies: a normal fibroblast cell line designated HSF, BALB/MK keratinocytes, a microvascular endothelial line designated Ea.hy.926, and a macrophage cell line designated J774.A1. The four cell lines are examined for in vitro uptake of LDL-ce6, Mal-BSA-ce6, and nanospherece6 conjugates. Variables tested are concentration of conjugate, incubation time, and comparison of uptake at 37° and 40° C., to measure internalization.

Concentrations of conjugate and incubation time will be chosen for a light dose-cell survival response curve. Doses of PDT are administered to give survivals of 95%, 75%, 50%, and 25%. At various time points after PDT (1, 6, and 24 hours), cells are harvested. Total RNA is extracted and assayed for the presence of mRNA coding for TGF$\beta$, VEGF, and IGF by Northern hybridization. Controls receiving conjugate alone or light alone are also tested for comparison. An immunofluorometric assay for VEGF in culture supernatant, which is capable of detecting 10 femtomoles of VEGF is used (Detmar et al., *J. Invest. Dermatol.* 105:44–50 (1995)). The culture supernatant from PDT-treated macrophages is tested to see if it is capable of inducing the expression of VEGF by fibroblasts and keratinocytes, and if it has any mitogenic effect on their growth rate. Similarly, the culture supernatant of treated fibroblasts and keratinocytes is tested to see if it has a mitogenic effect on microvascular endothelial cells.

Three wound models are used for in vivo testing. One model is a rabbit ear excisional model, which produces an avascular ulcer which can only heal from the edges. The second model is an FEL induced wound model on the rat dorsum. Intravenous and perilesional injection is compared for doses ranging from 50 $\mu$g to 1 mg/kg of ce6 equivalent. Various times are allowed for macrophage accumulation of conjugate (1, 6, and 24 hours). In vivo fluorescence imaging is carried out by the two photon confocal fluorescence system. The lesions are irradiated with varying fluences of 666 nm light with appropriate controls. The rate of formation of granulation tissue, and re-epithelization is measured. Punch biopsies (2 mm) for total RNA extraction and analysis of TGF$\beta$, IGF, and VEGF mRNA by Northern hybridization are taken at early and late time points. At 3, 7, and 14 days post treatment, animals are sacrificed and the wounds removed. Strips of the wounds are removed and their strength is measured with a tensometer. Cross sections of the wounds are removed and analyzed histologically. They are stained by immunoperoxidase techniques to quantitate the number of macrophages, endothelial cells, and myofibroblasts.

For studies on photodynamic therapy for abdominal adhesions, a third model, the rat model described by Langer et al. (*J. Surg. Res.* 59: 344–348 (1995)), is employed. In that model, rats develop intra-abdominal adhesions that can be graded from grade 1 (thin easily separable) to grade 3 (extensive dense tissue masses) (Elkins et al., *Fertil. Steril.* 41: 926–928 (1984). Intra-abdominal photodynamic therapy is performed using methods described by Molpus et al. (*Cancer Res.* 56:1075–1082 (1996)) for treatment of experimental ovarian cancer. Photosensitizers or conjugates are injected intraperitoneally, followed by administration of red light. The red light is administered through an optical fiber that penetrates the abdominal wall and into a peritoneal cavity, which has been filled with intralipid as a light diffuser. To test whether intra-abdominal PDT can positively affect the degree of adhesion formation, four variables are investigated: (1) light dose, (2) conjugate dose, (3) time between cecal injury and the treatment, and (4) time between i.p injection of conjugate and the delivery of i.p. light. These parameters are varied systematically. Rats are sacrificed four weeks after treatment, and their adhesions are graded in a blind experimental design. Samples of the adhesion tissue are removed for histological staining.

Other embodiments are within the following claims.

We claim:

1. A method for inhibiting fibrosis in the healing of a wound in a mammal, comprising:
    (a) administering to a mammal that has an unhealed or partially-healed wound an effective amount of a photosensitizer targeted to macrophages or myofibroblasts by conjugation of a targeting moiety;

(b) waiting for a time period wherein said photosensitizer reaches an effective tissue concentration at the wound site;

(c) photoactivating said photosensitizer at said wound site by delivering specifically to said wound site light of an effective wavelength and intensity, for an effective length of time, wherein the dose of photodynamic therapy is sufficient to kill from about 10% to about 90% of the targeted cells exposed to photoactivating light, thereby inhibiting fibrosis in said healing of said wound in said mammal.

2. The method of claim 1, wherein said photosensitizer is selected from the group consisting of: porphyrins, chlorins, bacteriochlorins, purpurins, phthalocyanines, naphthalocyanines, texaphyrins, and non-tetrapyrrole photosensitizers.

3. The method of claim 1, wherein said targeting moiety is selected from the group consisting of a protein, a peptide and a microparticle.

4. The method of claim 1, wherein the administration of said photosensitizer is systemic.

5. The method of claim 4, wherein said administration is at a dosage level between about 0.1 mg/kg and about 50 mg/kg.

6. The method of claim 5, wherein said administration is at a dosage level between about 0.5 mg/kg and about 10 mg/kg.

7. The method of claim 1, wherein the administration said photosensitizer is local.

8. The method of claim 7, wherein said administration is parenteral.

9. The method of claim 7, wherein said administration is topical.

10. The method of claim 1, wherein said photoactivating step comprises delivering light by means of optical fibers.

11. The method of claim 1, wherein said photoactivating step comprises delivering light by means of transillumination.

12. The method of claim 1, wherein said photoactivating step comprises delivering light by means of open arthrotomy.

13. The method of claim 1, wherein said photoactivating step comprises delivering laser light.

14. The method of claim 1, wherein said inhibition is performed prophylactically, prior to surgery, to reduce surgical adhesions.

* * * * *

UNITED STATES PATENT AND TRADEMARK OFFICE
CERTIFICATE OF CORRECTION

PATENT NO.5,913,884

DATED: JUNE 22, 1999

INVENTOR(S): KENNETH TRAUNER ET AL.

It is certified that error appears in the above-identified patent and that said Letters Patent is hereby corrected as shown below:

Column 1, line 8, before "Background of the Invention", please insert –

Statement as to Federally Sponsored Research

This invention was made, at least in part, with funds provided by the United States Navy Grant Number N 00014-94-I-0927, and the United States government therefore has certain rights in the invention.--

Signed and Sealed this

Twentieth Day of March, 2001

*Attest:*

NICHOLAS P. GODICI

*Attesting Officer*  *Acting Director of the United States Patent and Trademark Office*

UNITED STATES PATENT AND TRADEMARK OFFICE
CERTIFICATE OF CORRECTION

PATENT NO. : 5,913,884
DATED : June 22, 1999
INVENTOR(S) : Kenneth Trauner et al.

It is certified that error appears in the above-identified patent and that said Letters Patent is hereby corrected as shown below:

Column 1,
Line 11, after "United States Navy Grant Number N 00014-94-I-0927," please insert
-- This invention was made with Government support Grant No. DE-FG02-94ER61228 awarded by the U.S. Department of Energy. The Government has certain rights in this invention. --

Signed and Sealed this

Fourth Day of January, 2005

JON W. DUDAS
*Director of the United States Patent and Trademark Office*